US011944711B2

(12) United States Patent
Satou

(10) Patent No.: US 11,944,711 B2
(45) Date of Patent: Apr. 2, 2024

(54) SANITIZING SYSTEM FOR VEHICLE

(71) Applicant: Yazaki Corporation, Tokyo (JP)

(72) Inventor: Kazuya Satou, Makinohara (JP)

(73) Assignee: Yazaki Corporation, Tokyo (JP)

( * ) Notice: Subject to any disclaimer, the term of this patent is extended or adjusted under 35 U.S.C. 154(b) by 329 days.

(21) Appl. No.: 17/185,228

(22) Filed: Feb. 25, 2021

(65) Prior Publication Data

US 2021/0260229 A1 Aug. 26, 2021

(30) Foreign Application Priority Data

Feb. 25, 2020 (JP) ................................ 2020-029773
Aug. 5, 2020 (JP) ................................ 2020-133240

(51) Int. Cl.
*A61L 2/10* (2006.01)
*A61L 2/24* (2006.01)

(52) U.S. Cl.
CPC *A61L 2/10* (2013.01); *A61L 2/24* (2013.01); *A61L 2202/14* (2013.01); *A61L 2202/25* (2013.01)

(58) Field of Classification Search
CPC .......... A61L 2/10; A61L 2/24; A61L 2202/14; A61L 2202/25; B60Q 3/68; B60Q 3/80; B60Q 3/82; B60H 3/0071
See application file for complete search history.

(56) References Cited

U.S. PATENT DOCUMENTS 10,137,825 B1 * 11/2018 Salter ...................... F21S 45/47
2009/0117001 A1 5/2009 Hyde et al.
2014/0226303 A1 * 8/2014 Pasdar ..................... B60Q 3/18 362/23.08
2015/0273093 A1 * 10/2015 Holub ..................... B60Q 3/68 250/492.1
2017/0080117 A1 * 3/2017 Gordon .................. A61L 2/084
2017/0129396 A1 5/2017 Salter et al.
2019/0076558 A1 3/2019 Zhang-Miske et al.
2019/0142981 A1 5/2019 Kim et al.
2019/0240370 A1 * 8/2019 Benedek ............. B01D 53/007
2020/0055450 A1 * 2/2020 Drbohlav ................ B60Q 3/68

(Continued)

FOREIGN PATENT DOCUMENTS

JP 2006-341759 A 12/2006
JP 20100209513 A 9/2010
JP 2012-254673 A 12/2012

(Continued)

*Primary Examiner* — Jennifer Wecker
*Assistant Examiner* — Brady C Pilsbury
(74) *Attorney, Agent, or Firm* — Banner & Witcoff, Ltd.

(57) ABSTRACT

A sanitizing system for a vehicle includes an ultraviolet light source mounted on the vehicle and configured to irradiate an irradiation target with an ultraviolet ray so as to sanitize the irradiation target and a control unit configured to control the ultraviolet light source to be turned on and off. The sanitizing system may further include an illumination light source configured to illuminate the irradiation target of the ultraviolet light source. The control unit may turn on the illumination light source when the ultraviolet light source is turned on. The control unit may be configured to carry out a first detection that an occupant outside the vehicle approaches the vehicle and turn on the ultraviolet light source in response to the first detection.

6 Claims, 7 Drawing Sheets

| | STOP OF VEHICLE | OCCUPANT APPROACHES VEHICLE | IMMEDIATELY BEFORE BOARDING | ON BOARD | GETTING OFF |
|---|---|---|---|---|---|
| DEEP ULTRAVIOLET LED | OFF | ON | OFF | ・TURNED ON BY SANITIZING SWITCH<br>・TEMPORARY LIGHTING BY SWITCHING FROM SEATING TO SEAT-LEAVING | TEMPORARY LIGHTING |
| ILLUMINATION LED | OFF | ON | OFF | ・TURNED ON BY SANITIZING SWITCH<br>・TURNED ON BY ILLUMINATION SWITCH<br>・TEMPORARY LIGHTING BY SWITCHING FROM SEATING TO SEAT-LEAVING | TEMPORARY LIGHTING |

(56) References Cited

U.S. PATENT DOCUMENTS

| | | | |
|---|---|---|---|
| 2020/0138990 | A1 | 5/2020 | Kim et al. |
| 2021/0244383 | A1 | 8/2021 | Wang |

FOREIGN PATENT DOCUMENTS

| | | | | |
|---|---|---|---|---|
| JP | 2017-029293 A | | 2/2017 | |
| JP | 2018-525063 A | | 9/2018 | |
| KR | 1998-0041402 U | | 9/1998 | |
| KR | 0178167 B1 | * | 4/1999 | ............... B60Q 3/68 |
| KR | 2013-0021747 A | | 3/2013 | |

* cited by examiner

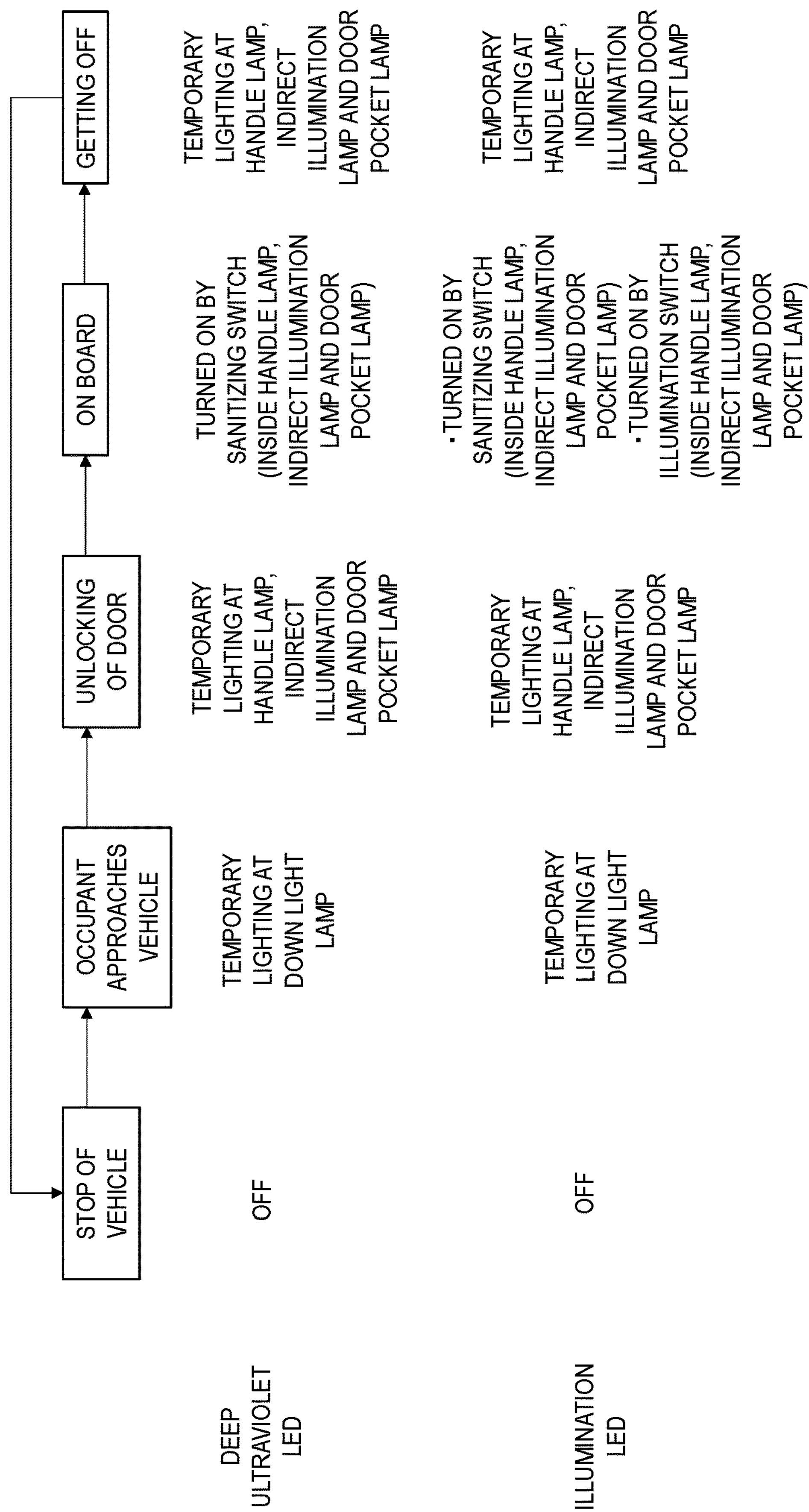
FIG. 7
STOP OF VEHICLE
OCCUPANT APPROACHES VEHICLE
UNLOCKING OF DOOR
ON BOARD
GETTING OFF
DEEP ULTRAVIOLET LED
OFF
TEMPORARY LIGHTING AT DOWN LIGHT LAMP
TEMPORARY LIGHTING AT HANDLE LAMP, INDIRECT ILLUMINATION LAMP AND DOOR POCKET LAMP
TURNED ON BY SANITIZING SWITCH (INSIDE HANDLE LAMP, INDIRECT ILLUMINATION LAMP AND DOOR POCKET LAMP)
TEMPORARY LIGHTING AT HANDLE LAMP, INDIRECT ILLUMINATION LAMP AND DOOR POCKET LAMP
ILLUMINATION LED
OFF
TEMPORARY LIGHTING AT DOWN LIGHT LAMP
TEMPORARY LIGHTING AT HANDLE LAMP, INDIRECT ILLUMINATION LAMP AND DOOR POCKET LAMP
·TURNED ON BY SANITIZING SWITCH (INSIDE HANDLE LAMP, INDIRECT ILLUMINATION LAMP AND DOOR POCKET LAMP)
·TURNED ON BY ILLUMINATION SWITCH (INSIDE HANDLE LAMP, INDIRECT ILLUMINATION LAMP AND DOOR POCKET LAMP)
TEMPORARY LIGHTING AT HANDLE LAMP, INDIRECT ILLUMINATION LAMP AND DOOR POCKET LAMP

SANITIZING SYSTEM FOR VEHICLE

CROSS-REFERENCE TO RELATED APPLICATION

The present application claims priority to Japanese Patent Applications No. 2020-29773 filed on Feb. 25, 2020 and No. 2020-133240 filed on Aug. 5, 2020, the entire content of which is incorporated herein by reference.

TECHNICAL FIELD

The present invention relates to a sanitizing system for a vehicle, which sanitizes inside of the vehicle.

BACKGROUND

Inside of a vehicle is sanitized, in general, by spraying a sanitizer such as alcohol on a seat. However, in that case, an operation of spraying the sanitizer is required, which requires time and effort. Therefore, an air purifier by which sanitizing ions are blown out into an interior of a vehicle has been proposed (for example, see JP2006-341759A), but the air purifier described above requires periodic filter replacement.

SUMMARY

Illustrative aspects of the present invention provide a sanitizing system for a vehicle configured to easily sanitize inside of the vehicle without requiring too much time and effort.

According to an illustrative aspect of the present invention, a sanitizing system for a vehicle includes an ultraviolet light source mounted on the vehicle and configured to irradiate an irradiation target with an ultraviolet ray so as to sanitize the irradiation target and a control unit configured to control the ultraviolet light source to be turned on and off.

Other aspects and advantages of the invention will be apparent from the following description, the drawings and the claims.

BRIEF DESCRIPTION OF DRAWINGS

FIG. 7 is an explanatory diagram for explaining an operation of the vehicle lighting system shown in FIGS. 4 and 5.

DESCRIPTION OF EMBODIMENTS

An embodiment according to the present invention will be described below with reference to the drawings.

Figure 1:
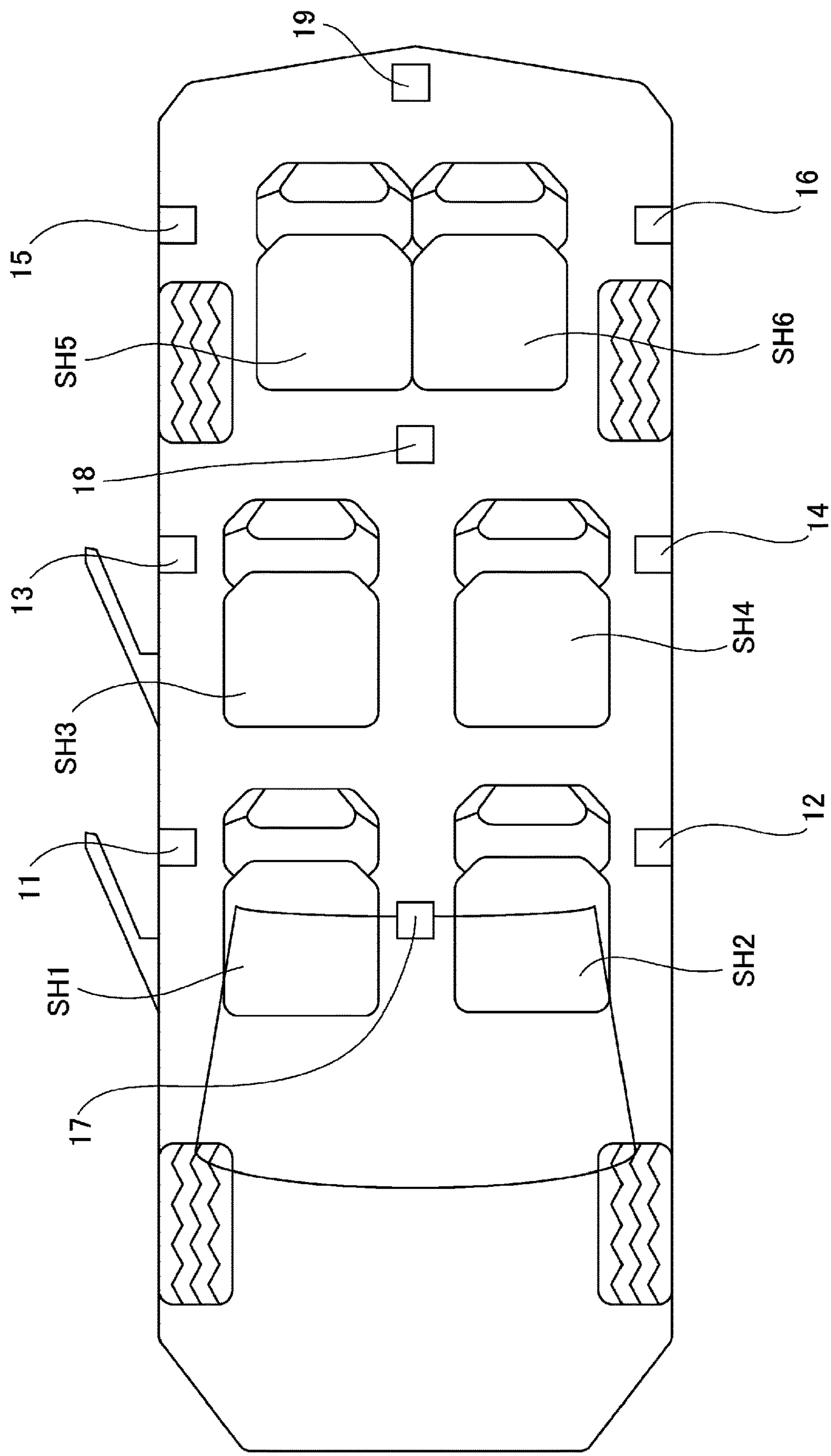
FIG. 1 is a schematic view of a vehicle equipped with a vehicle lighting system as a sanitizing system for the vehicle according to an embodiment of the present invention.

A vehicle lighting system 1 described above is a system mounted on a vehicle to illuminate an interior of the vehicle. In the present embodiment, as shown in FIG. 1, a three-row seat vehicle in which a driver seat SH1, a front passenger seat SH2, a right seat SH3 in a second row, a left seat SH4 in the second row, a right seat SH5 in a third row and a left seat SH6 in the third row (these may be collectively referred to as "seats SH1 to SH6") are mounted will be described as an example of the vehicle. However, the number of seats of the vehicle is not limited thereto.

The vehicle lighting system 1 includes personal lamps 11 to 16, dome lamps 17, 18, and a luggage lamp 19. These lamps 11 to 19 are provided on a ceiling of the vehicle. The personal lamps 11 to 16 are provided for the respective seats SH1 to SH6, and individually illuminate the seats SH1 to SH6. The dome lamps 17, 18 are disposed at a center of the ceiling in a width direction of the vehicle and illuminate the entire interior of the vehicle. In the present embodiment, two dome lamps 17, 18 are provided side by side along a front-rear direction of the vehicle. The luggage lamp 19 is disposed at a rear portion of the ceiling and illuminates a luggage room.

Figure 2:
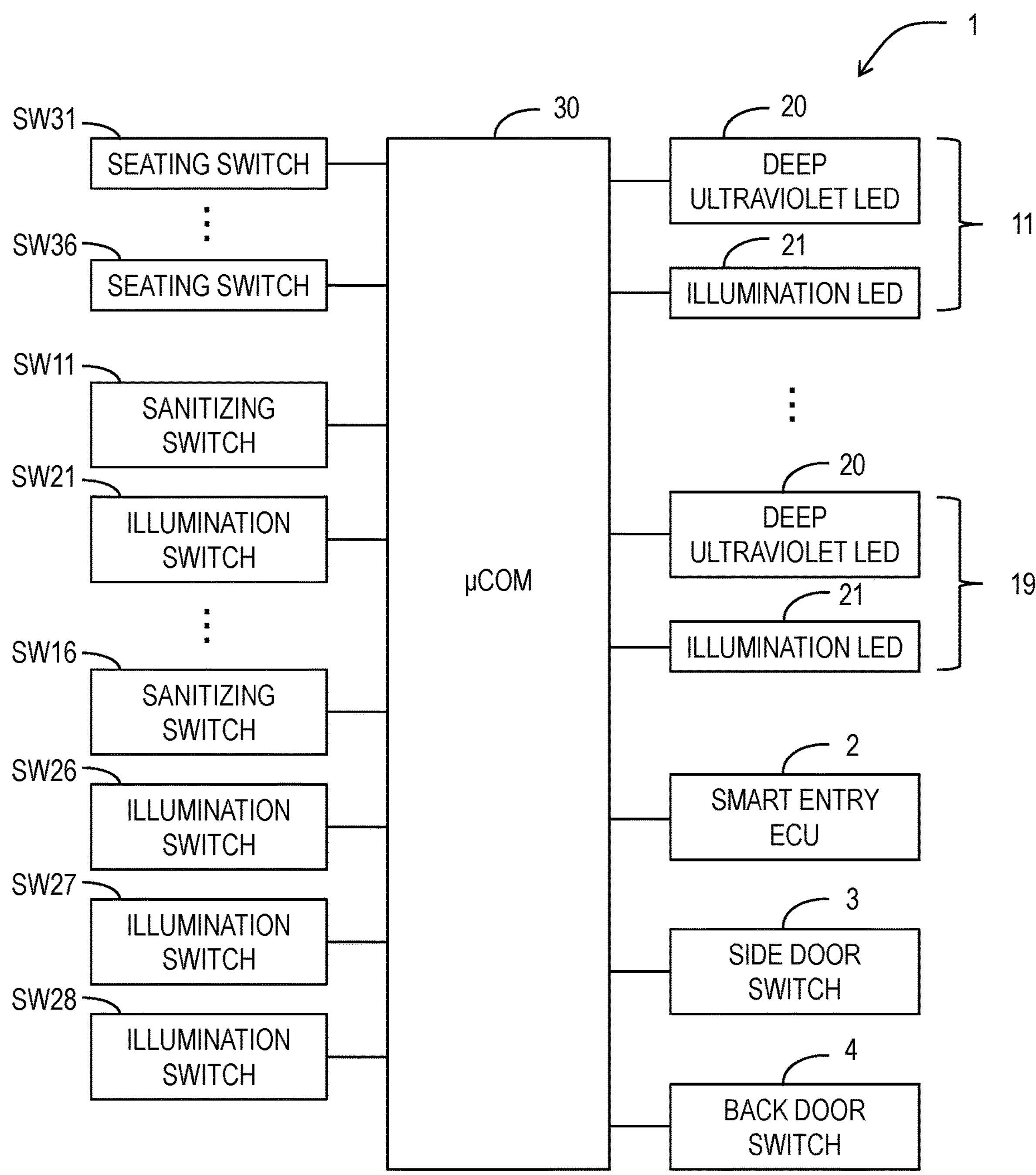
FIG. 2 is an example of an electrical configuration diagram of the vehicle lighting system shown in FIG. 1.

As shown in FIG. 2, each of the lamps 11 to 19 includes a deep ultraviolet LED 20 (an ultraviolet light source) and an illumination LED 21 (an illumination light source). The deep ultraviolet LED 20 emits a deep ultraviolet ray belonging to a region having a short wavelength among ultraviolet rays. The deep ultraviolet ray has a high sanitizing ability, and sanitizes an irradiation target. In the present embodiment, irradiation targets of the personal lamps 11 to 16 are respectively the seats SH1 to SH6. For this reason, the deep ultraviolet LED 20 of each of the personal lamps 11 to 16 sanitizes each of the seats SH1 to SH6. The deep ultraviolet ray is not in a visible light region, and cannot be visually recognized by human eyes.

The illumination LED 21 emits visible light to illuminate the irradiation target. In the present embodiment, the illumination LED 21 is formed of a full-color LED, and emits light in full color. The irradiation targets (irradiation ranges) of the deep ultraviolet LED 20 and the illumination LED 21 are the same.

The vehicle lighting system 1 includes a microcomputer (μCOM) 30 configured to control an entire system. The μCOM 30 (a control unit) has a well-known CPU, ROM and RAM, and the CPU is configured to operate according to a program stored in the ROM. The lamps 11 to 19 are connected to the μCOM 30, and the μCOM 30 is configured to individually control these lamps 11 to 19 and individually control the deep ultraviolet LED 20 and the illumination LED 21 of each of the lamps 11 to 19.

As shown in FIG. 2, the μCOM 30 of the vehicle lighting system 1 is configured to communicate with a smart entry ECU 2 configured to control an entire smart entry system. The smart entry ECU 2 is an ECU configured to control a door lock mechanism based on wireless communication with a smart key, an operation state of an operation unit provided in a door handle, or the like. Specifically, the smart entry ECU 2 can detect that an occupant who owns the smart key is in vicinity of the vehicle outside the vehicle by the wireless communication with the smart key. When detecting a lock operation and an unlock operation by the operation unit during the detection, the smart entry ECU 2 controls the door lock mechanism to lock and unlock a door. The smart entry ECU 2 transmits, to the μCOM 30, information indicating the detection that the occupant is in the vicinity of the vehicle outside the vehicle, information indicating that the door is locked, information indicating that the door is unlocked, and the like.

The μCOM 30 is connected to a side door switch 3 that is turned on and off in response to opening and closing of a side door, and a back door switch 4 that is turned on and off in response to opening and closing of a back door. The μCOM 30 can detect an open or closed state of the door by detecting an on or off state of these switches 3, 4.

In addition, the vehicle lighting system 1 includes sanitizing switches SW11 to SW16 (switches), each of which turns on and off the deep ultraviolet LED 20 of each of the personal lamps 11 to 16 (sanitizing operation), and illumination switches SW21 to SW28, each of which turns on and off the illumination LED 21 of each of the personal lamps 11 to 16 and the dome lamps 17, 18. The sanitizing switches SW11 to SW16 are provided corresponding to the personal lamps 11 to 16, and can independently turn on and off the deep ultraviolet LED 20 of each of the personal lamps 11 to 16. The illumination switches SW21 to SW28 are provided corresponding to the personal lamps 11 to 16 and the dome lamps 17, 18, and can independently turn on and off the illumination LED 21 of each of the personal lamps 11 to 16 and the dome lamps 17, 18.

The μCOM 30 is connected to seating switches SW31 to SW36 that are respectively provided on the seats SH1 to SH6 and are turned on and off in response to seating and leaving seat by the occupants on the seats SH1 to SH6. The μCOM 30 is configured to detect the seating or leaving seat by the occupants on the seats SH1 to SH6 by detecting an on or off state of these switches SW31 to SW36.

Figure 3:
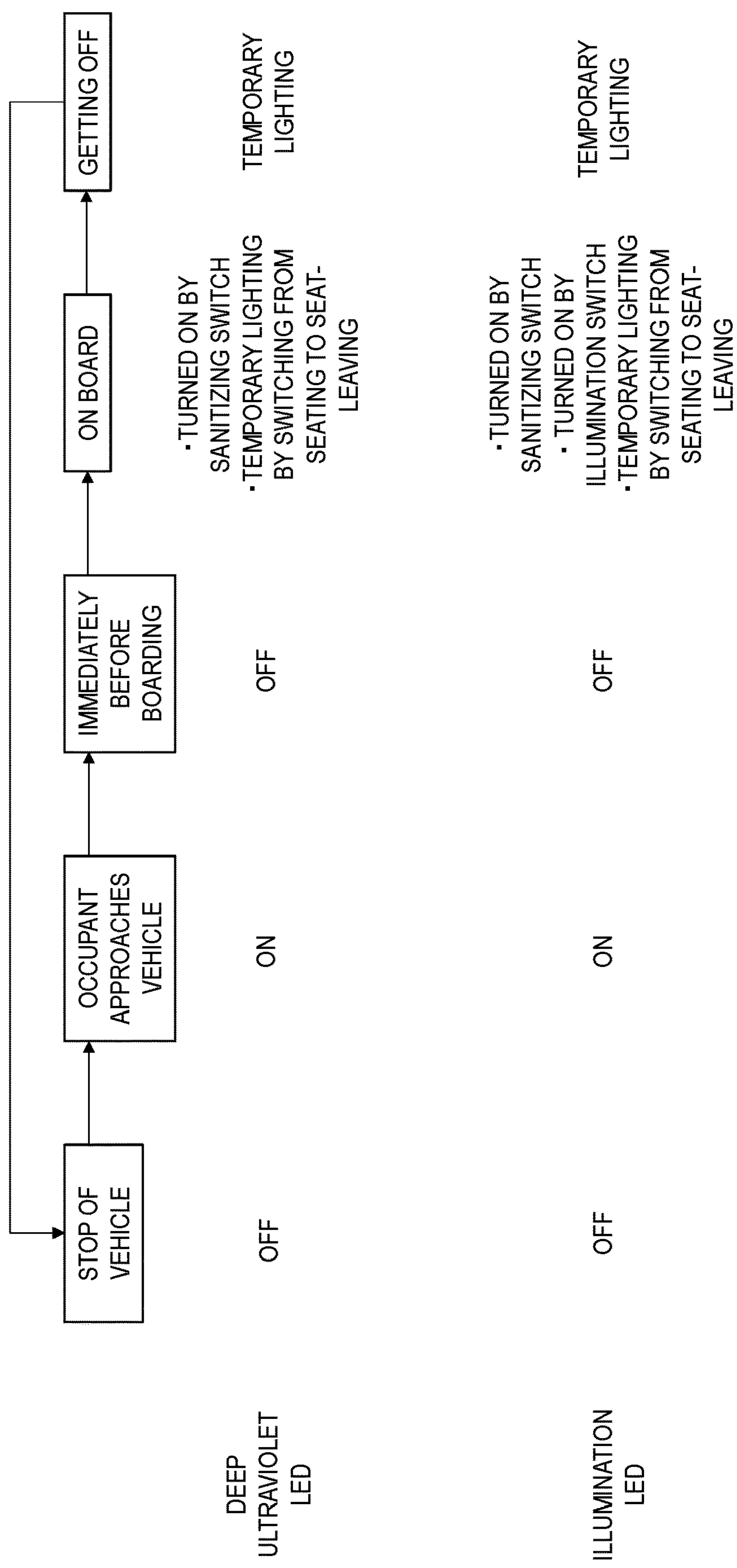
FIG. 3 is an explanatory diagram for explaining an operation of the vehicle lighting system shown in FIG. 1.

Next, an operation of the vehicle lighting system 1 having a configuration described above will be described with reference to FIG. 3. The μCOM 30 turns off the deep ultraviolet LED20 and the illumination LED21 of all the lamps 11 to 16 during a stop of the vehicle when the occupant gets off and no one is on board. The μCOM 30 functions as/has a first detection unit configured to carry out a first detection. The first detection is to detect that the occupant approaches the vehicle. The μCOM 30 or the first detection unit turns on the deep ultraviolet LED 20 and the illumination LED 21 of all the lamps 11 to 19 in response to the first detection, i.e., when a state in which the occupant approaches the vehicle is detected. At this time, the μCOM 30 turns on the illumination LED 21 in a color (for example, blue) indicating that sanitizing is being performed. By turning on the illumination LED 21, the occupant can know that sanitizing is being performed before the occupant gets on board.

In the present embodiment, the μCOM 30 detects that the occupant approaches the vehicle for boarding based on the information from the smart entry ECU 2. Specifically, when detecting that the occupant is in the vicinity of the vehicle outside the vehicle based on the information from the smart entry ECU 2 while determining that the door is locked based on the information from the smart entry ECU 2, the μCOM 30 detects that the occupant approaches the vehicle.

Thereafter, the μCOM 30 functions as/has a third detection unit configured to carry out a third detection. The third detection is to detect that the occupant is about to get on the vehicle, that is, a state of immediately before boarding. The μCOM 30 or the third detection unit turns off the deep ultraviolet LED 20 and the illumination LED 21 of all the lamps 11 to 19 in response to the third detection, i.e., when a state in which the occupant is about to get on the vehicle is detected.

In the present embodiment, after turning on the lamps 11 to 19 in response to the detection that the occupant approaches the vehicle, and for example, when it is determined that the door is opened based on the on or off state of the door switches 3, 4, the μCOM 30 detects the state of immediately before boarding. Also, the μCOM 30 may detect the state of immediately before boarding when determining that the occupant has performed the unlock operation of the door handle based on the information from the smart entry ECU2. In these cases, when the occupant approaches the vehicle, the lamps 11 to 19 start to light up, and when the door is opened for boarding, the lamps 11 to 19 are turned off. Therefore, a possibility that the occupant is irradiated with the ultraviolet ray can be reduced.

When the occupant turns on and off the illumination switches SW21 to SW28 while on board, the μCOM 30 turns on and off only the illumination LED 21 of each of the lamps 11 to 18 corresponding to the operated illumination switches SW21 to SW28. When the occupant turns on and off any one (ones) of the sanitizing switches SW11 to SW16 for (a) vacant seat(s), the one or ones of the sanitizing switches SW11 to SW16 being provided corresponding to the vacant seat(s) SH1 to SH6, the μCOM 30 turns on and off both the deep ultraviolet LED 20 and the illumination LED 21 of each of the lamps 11 to 16 corresponding to the operated sanitizing switch(es) SW11 to SW16. When the deep ultraviolet LED 20 is turned on, the μCOM 30 turns on the illumination LED 21 in a color (for example, blue) indicating that sanitizing is being performed. When detecting that the back door is opened based on the on or off state of the back door switch 4, the μCOM 30 turns on only the illumination LED 21 of the luggage lamp 19.

While on board, the μCOM 30 is configured to monitor the on or off state of the seating switches SW31 to SW36. The μCOM 30 functions as/has a fourth detection unit configured to carry out a fourth detection. The fourth detection is to detect either one of the following at a time; a first state in which the occupant sits on the seat and a second state in which the occupant has left the seat, i.e., the occupant is not present on the seat. The μCOM 30 or the fourth detection unit is configured to perform temporary lighting for turning on the corresponding lamps 11 to 19 for a certain period of time in response to a change in the fourth detection from the first state or a seating detection (a state in which seating of the occupant is being detected) to the second state or a seat-leaving detection (a state in which leaving the seat by the occupant is being detected) on the seats SH1 to SH6. Thereby, for example, when a hired taxi arrives at a destination and a customer gets off the vehicle, the seats SH2 to SH6 on which the customer has been seated can be automatically sanitized.

Thereafter, the μCOM 30 functions as/has a second detection unit a second detection unit configured to carry out a second detection. The second detection is to detect that all the occupants have got off the vehicle. The μCOM 30 or the second detection unit performs the temporary lighting for turning on the lamps 11 to 19 only for a certain period in response to the second detection, i.e., when a state in which all the occupants have got off the vehicle is detected. The μCOM 30 may detect getting-off (getting-off of all the occupants), i.e., carry out the second detection when the door gets closed after the door is opened while an ignition switch is off, and then the door is locked. In addition, the μCOM 30 may detect the getting-off based on the on or off state of the seating switches SW31 to SW36. Thereby, after all the occupants get off the vehicle, sanitizing can be performed automatically for a certain period of time. Even while the temporary lighting is being performed, the μCOM 30 turns off the lamps 11 to 19 upon detecting boarding.

According to the embodiment described above, the irradiation target is sanitized by being irradiated with the deep ultraviolet LED 20. Thereby, the inside of the vehicle can be easily sanitized without requiring too much time and effort by simply turning on the deep ultraviolet LED 20. In particular, even a vehicle used by an unspecified number of people a day (a vehicle for car sharing, for example) can be maintained in a clean state all the time.

According to the embodiment described above, the μCOM 30 turns on the illumination LED 21 that illuminates the irradiation target of the deep ultraviolet LED 20 when the deep ultraviolet LED 20 is turned on. Thereby, it is possible to notify the occupant that sanitizing is being performed by the ultraviolet ray.

According to the embodiment described above, the μCOM 30 turns on the deep ultraviolet LED 20 and the illumination LED 21 in response to the detection that the occupant approaches the vehicle. Thereby, welcome lighting with a sanitizing function can be performed.

Figure 4:
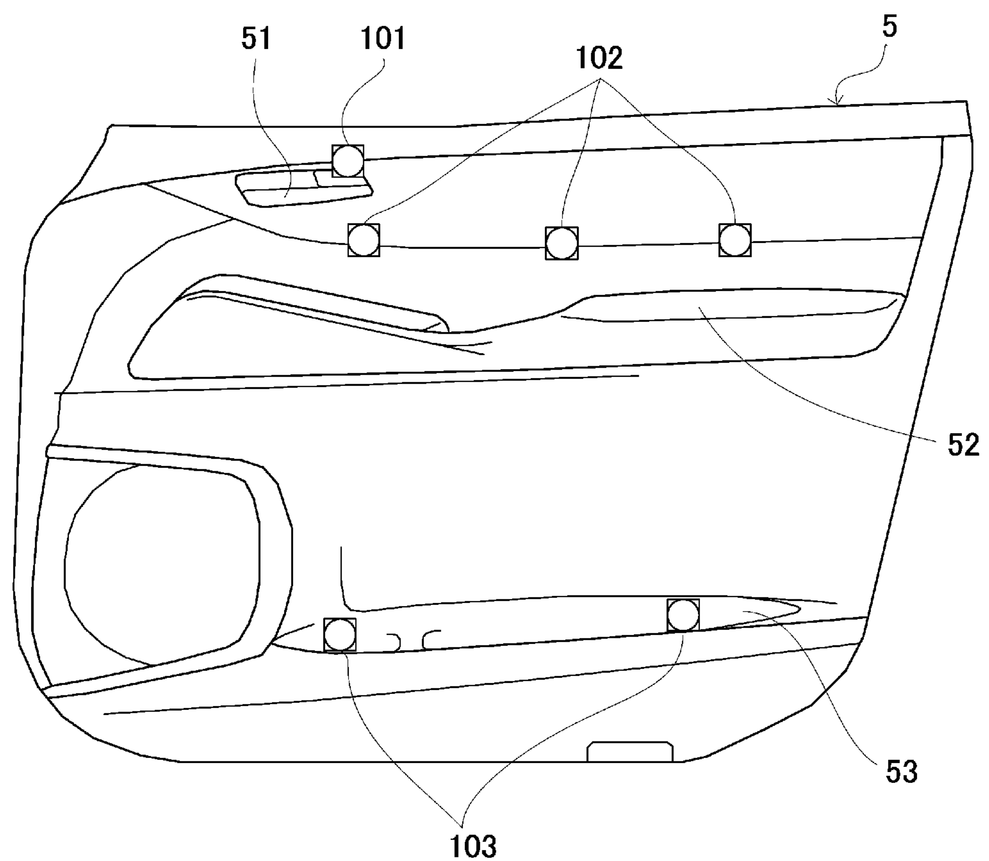
FIG. 4 is a partial schematic view of a vehicle equipped with a vehicle lighting system as a sanitizing system for the vehicle according to another embodiment of the present invention.

Next, another embodiment will be described. As shown in FIG. 4, in the another embodiment, the vehicle lighting system 1 further includes an inside handle lamp 101, an indirect illumination lamp 102 and a door pocket lamp 103 in addition to the lamps 11 to 19 described above. The lamps 101 to 103 are provided on a door trim 5 of inside of the door. The inside handle lamp 101 illuminates an inside handle 51. The indirect illumination lamp 102 indirectly illuminates an armrest 52 provided on the door trim 5. The door pocket lamp 103 illuminates inside of a door pocket 53 provided in the door trim 5.

Figure 5:
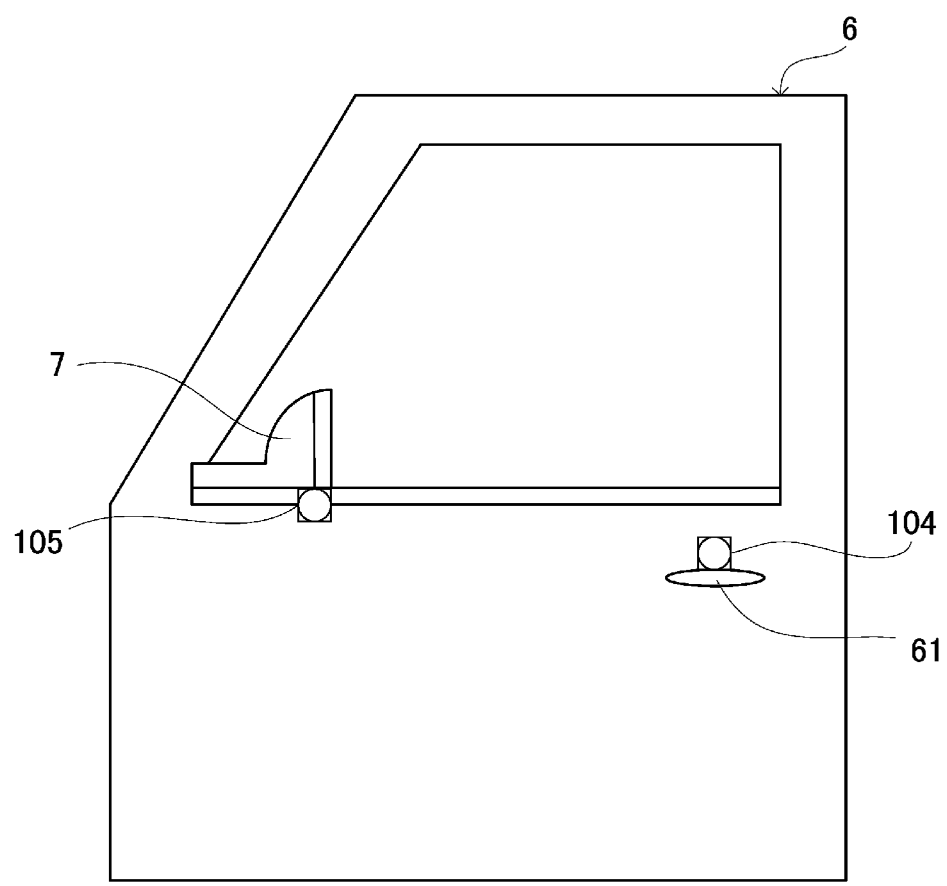
FIG. 5 is a partial schematic view of the vehicle equipped with the vehicle lighting system as the sanitizing system for the vehicle according to the another embodiment of the present invention.

As shown in FIG. 5, in the another embodiment, the vehicle lighting system 1 includes an outside handle lamp 104 and a downlight lamp 105. The outside handle lamp 104 is provided on outside of a door main body 6, which is outside of the door, and illuminates an outside handle 61. The downlight lamp 105 is provided on a lower side of a door mirror 7 and illuminates the lower side of the door mirror 7.

Figure 6:
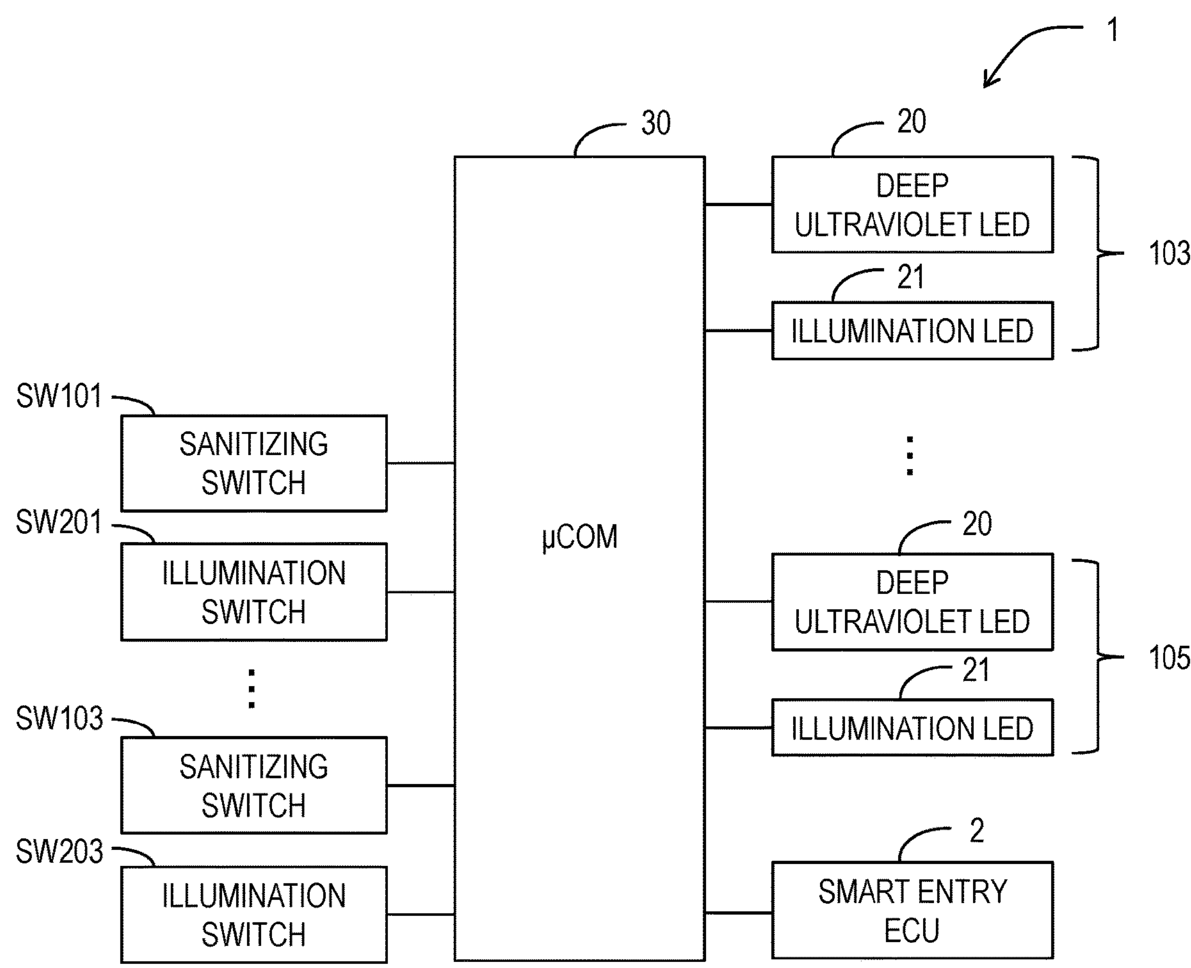
FIG. 6 is an example of an electrical configuration diagram of the vehicle lighting system shown in FIGS. 4 and 5.

As shown in FIG. 6, each of the lamps 101 to 105 includes the deep ultraviolet LED and the illumination LED 21 as in the former embodiment. The lamps 101 to 105 are connected to the μCOM 30. The μCOM 30 can individually control the lamps 101 to 105 and can individually control the deep ultraviolet LED 20 and the illumination LED 21 of each of the lamps 101 to 105.

In addition, the vehicle lighting system 1 includes sanitizing switches SW101 to SW103 (switches), each of which turns on and off the deep ultraviolet LED 20 of each of the lamps 101 to 103 installed in the interior of the vehicle (sanitizing operation), and illumination switches SW201 to SW203, each of which turns on and off the illumination LED 21 of each of the lamps 101 to 103. The sanitizing switches SW101 to SW103 are provided corresponding to the lamps 101 to 103, and can independently turn on and off the deep ultraviolet LED 20 of each of the lamps 101 to 103. The illumination switches SW201 to SW203 are provided corresponding to the lamps 101 to 103, and can independently turn on and off the illumination LED 21 of each of the lamps 101 to 103.

Next, control of the lamps 101 to 105 by the μCOM 30 described above will be described with reference to FIG. 7. The μCOM 30 turns off the deep ultraviolet LED 20 and the illumination LED 21 of the lamps 101 to 105 during a stop of the vehicle when the occupant gets off and no one is on board. When detecting that the occupant approaches the vehicle for boarding based on the information from the smart entry ECU 2, the μCOM 30 performs temporary lighting for turning on the deep ultraviolet LED 20 and the illumination LED 20 of the downlight lamp 105 for a certain period of time. Thereby, the occupant can sanitize his or her hand before boarding by holding his or her hand under the door mirror 7.

When the state of immediately before boarding is detected by detecting that the door is unlocked based on the information from the smart entry ECU 2, the μCOM 30 performs temporary lighting for turning on the deep ultraviolet LED 20 and the illumination LED 21 of each of the lamps 101 to 104 for a certain period of time. Thereby, the inside handle 51, the outside handle 61, the armrest 52 and the door pocket 53 that the occupant touches with hand can be sanitized immediately before boarding.

When the occupant turns on and off the illumination switches SW201 to SW203 while on board, the μCOM 30 turns on and turns off only the illumination LED 21 of each of the lamps 101 to 103 corresponding to the operated illumination switches SW201 to SW203. When the occupant turns on and off the sanitizing switches SW101 to SW103, the μCOM 30 turns on and off both the deep ultraviolet LED 20 and the illumination LED 21 of each of the lamps 101 to 103 corresponding to the operated sanitizing switches SW101 to SW103.

Thereafter, when detecting that the occupant gets off the vehicle by a method the same as in the former embodiment, the μCOM 30 performs temporary lighting in which the lamps 101 to 104 are turned on for a certain period of time.

According to the embodiment described above, the μCOM 30 turns on the deep ultraviolet LED 20 of each of the lamps 101 to 104 provided on the door to sanitize the door in response to the detection that occupant gets on board. Thereby, the door can be sanitized when the occupant gets on board.

While the present invention has been described with reference to certain exemplary embodiments thereof, the scope of the present invention is not limited to the exemplary embodiments described above, and it will be understood by those skilled in the art that various changes and modifications may be made therein without departing from the scope of the present invention as defined by the appended claims.

In the embodiment described above, the illumination LED 21 is formed of a full-color LED, but the present invention is not limited thereto. The illumination LED 21 may be any one that emits visible light, and may be one that emits light in a single color.

In the embodiment described above, the illumination LED 21 is always turned on when the deep ultraviolet LED 20 is turned on, but the present invention is not limited thereto. Only the deep ultraviolet LED 20 may be turned on, or the occupant may be able to select whether to turn on the illumination LED 21.

A fluorescent material may be provided on the irradiation target by applying a fluorescent paint or the like so that the fluorescent material emits light when being irradiated with the deep ultraviolet LED 20, thereby making it possible to visually recognize that sanitization is being performed.

According to the embodiment described above, an example in which the vehicle lighting system 1 is mounted on the vehicle employing the smart entry system that locks and unlocks the door when the occupant who owns the smart key operates the operation unit provided in the door handle has been described, but the present invention is not limited thereto. Some smart entry systems are configured to unlock a door by only a smart key approaching a vehicle while the door is locked, and to lock the door by only the smart key moving away from the vehicle when the door is not locked. The vehicle lighting system 1 may be mounted on the vehicle employing such a smart entry system.

According to the embodiment described above, the μCOM 30 and the smart entry electronic control unit (ECU) 2 can communicate with each other in order to detect that the occupant approaches the vehicle, but the present invention is not limited thereto. In the vehicle employing keyless entry, a keyless entry ECU and the μCOM 30 may be able to communicate with each other to detect that the occupant approaches the vehicle. The keyless ECU performs wireless communication with a keyless key (smart key), and when detecting a lock operation and an unlock operation of the keyless key, the keyless ECU locks and unlocks the door. The μCOM may detect that the occupant approaches the vehicle when it is determined that the unlock operation of the keyless key is performed by communicating with the keyless ECU.

According to the embodiment described above, the deep ultraviolet LED 20 that emits the deep ultraviolet ray is used as the ultraviolet light source. However, the ultraviolet light source may be any one that irradiates an ultraviolet ray, and is not limited to one that irradiates a deep ultraviolet ray.

According to an aspect of the embodiments described above, a sanitizing system for a vehicle (1) includes an ultraviolet light source (20) mounted on the vehicle and configured to irradiate an irradiation target with an ultraviolet ray so as to sanitize the irradiation target and a control unit (30) configured to control the ultraviolet light source (20) to be turned on and off.

According to the sanitizing system for the vehicle having above described configuration, the irradiation target is sanitized by being irradiated with the ultraviolet ray from the ultraviolet light source. Thereby, the inside of the vehicle can be easily sanitized without requiring too much time and effort by simply turning on the ultraviolet light source.

The sanitizing system for the vehicle (1) may further include an illumination light source (21) configured to illuminate the irradiation target of the ultraviolet light source (20). The control unit (30) may turn on the illumination light source (21) when the ultraviolet light source (20) is turned on.

With this configuration, the control unit turns on the illumination light source configured to illuminate the irradiation target of the ultraviolet light source when the ultraviolet light source is turned on. Thereby, it is possible to notify the occupant that sanitizing is performed by the ultraviolet ray.

The irradiation target may be provided with a fluorescent material which emits light by irradiation with the ultraviolet ray.

With this configuration, the fluorescent material provided on the irradiation target emits light when the ultraviolet light source is turned on. Thereby, it is possible to notify the occupant that sanitizing is being performed by the ultraviolet ray.

The control unit (30) may be configured to carry out a first detection that an occupant outside the vehicle approaches the vehicle and turn on the ultraviolet light source (20) in response to the first detection.

With this configuration, the control unit turns on the ultraviolet light source in response to the detection (first detection) by the first detection unit that the occupant approaches. Thereby, sanitizing by the ultraviolet light source can be performed before the occupant gets on board.

The control unit (30) may be configured to carry out a second detection that the occupant has got off the vehicle and turn on the ultraviolet light source (20) in response to the second detection.

With this configuration, the control unit turns on the ultraviolet light source in response to the detection (second detection) by the second detection unit that the occupant has got off the vehicle. Thereby, sanitizing by the ultraviolet light source can be performed after the occupant gets off the vehicle.

The control unit (30) may be configured to carry out a third detection that the occupant is about to get on board and turn off the ultraviolet light source (20) in response to the third detection.

With this configuration, the control unit turns off the ultraviolet light source in response to the detection (third detection) by the third detection unit that occupant is about to get on board. Thereby, the ultraviolet light source can be turned off when the occupant gets on board.

The sanitizing system for the vehicle (1) may further include a switch (SW11 to SW16) configured to be operated by the occupant. The control unit (30) may turn on the ultraviolet light source (20) in response to the operation of the switch (SW11 to SW16) by the occupant.

With this configuration, the occupant can turn on the ultraviolet light source by operating the switch.

The irradiation target may be a seat in the vehicle. The control unit (30) may be configured to carry out a fourth detection of a first state in which the occupant sits on the seat and a second state in which the occupant has left the seat and turn on the ultraviolet light source (20) in response to a change in the fourth detection from the first state to the second state.

With this configuration, when the occupant leaves the seat, the seat can be automatically sanitized by being irradiated with the ultraviolet ray.

The irradiation target may be a door. The control unit (30) may configured to carry out a third detection that the occupant is about to get on board and turn on the ultraviolet light source (20) only for a certain period of time in response to the third detection.

With this configuration, the control unit turns on the ultraviolet light source to sanitize the door in response to the detection by the third detection unit that occupant is about to get on board. Thereby, the door can be sanitized when the occupant gets on board.

What is claimed is:

1. A sanitizing system for a vehicle including:

a plurality of lamps mounted at a plurality of positions in the vehicle, each of the lamps including:

an ultraviolet light source configured to irradiate an irradiation target with an ultraviolet ray so as to sanitize the irradiation target, and an illumination light source configured to illuminate the irradiation target of the ultraviolet light source and formed of a multi-color LED configured to emit a plurality of colors corresponding to a plurality of visible wavelengths different from one or more wavelengths of light emitted by the ultraviolet light source;

a control unit configured to control the ultraviolet light source and the illumination light source to be turned on and off; and an illumination switch configured to be operated by an occupant of the vehicle, wherein the control unit is further configured to:

turn on only the illumination light source corresponding to the operation of the illumination switch;

detect that the occupant outside the vehicle approaches the vehicle;

turn on the ultraviolet light source and the illumination light source in response to detecting that the occupant outside the vehicle approaches the vehicle;

detect that the occupant is about to get on board by determining that a door of the vehicle is opened after detecting that the occupant approaches the vehicle and after turning on the ultraviolet light source and the illumination light source; and subsequently turn off the ultraviolet light source and the illumination light source in response to detecting that the occupant is about to get on board by determining that the door of the vehicle is opened, wherein, when the ultraviolet light source is turned on, the illumination light source is turned on by turning on the multi-color LED in a color specific to and indicating that sanitizing is being performed.

2. The sanitizing system according to claim 1, the irradiation target is provided with a fluorescent material which emits light by irradiation with the ultraviolet ray.

3. The sanitizing system according to claim 1, wherein the control unit is configured to: carry out a second detection that an occupant has got off the vehicle; and turn on the ultraviolet light source in response to the second detection.

4. The sanitizing system according to claim 1, further including:

a switch configured to be operated by the occupant, wherein the control unit turns on the ultraviolet light source in response to the operation of the switch by the occupant.

5. The sanitizing system according to claim 1, wherein the irradiation target is a seat in the vehicle, wherein the control unit is configured to: detect a first state in which the control unit detects that the occupant is sitting on the seat and a second state in which the control unit detects that the occupant has left the seat; and turn on the ultraviolet light source in response to detecting a change from the first state to the second state.

6. The sanitizing system according to claim 1, wherein the irradiation target is a door of the vehicle.

* * * * *